(12) United States Patent
Sato et al.

(10) Patent No.: US 6,235,775 B1
(45) Date of Patent: May 22, 2001

(54) ACETONE ADDUCT OF FUNGICIDAL V-28-3M

(75) Inventors: Yutaka Sato; Yuuichi Aoki, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/525,320

(22) Filed: Mar. 13, 2000

Related U.S. Application Data

(63) Continuation of application No. PCT/JP98/04070, filed on Sep. 10, 1998.

(30) Foreign Application Priority Data

Sep. 12, 1997 (JP) .................................... 9-248093

(51) Int. Cl.⁷ ........................ C07D 315/00; A61K 31/35
(52) U.S. Cl. .......................................... 514/460; 549/415
(58) Field of Search .............................. 514/460; 549/415

(56) References Cited

U.S. PATENT DOCUMENTS

| 4,177,265 | 12/1979 | Michel et al. . |
| 5,023,079 | 6/1991 | Komoda et al. . |

FOREIGN PATENT DOCUMENTS

| 4-12199 | 4/1992 | (JP) . |
| 4-53878 | 8/1992 | (JP) . |
| 5-59084 | 3/1993 | (JP) . |

*Primary Examiner*—Deborah C. Lambkin
(74) *Attorney, Agent, or Firm*—Oblon, Spivak, McClelland, Maier & Neustadt, P.C.

(57) ABSTRACT

The present invention provides an acetone adduct of V-28-3M to be used as an intermediate for producing V-28-3M which is useful as a fungicide, a process for producing it and a process for purifying V-28-3M. When crude V-28-3M is dissolved in acetone, an acetone adduct of V-28-3M is to remarkably improve the crystallization rate and, accordingly, also to remarkably improve the purity. The obtained acetone adduct can be easily hydrolyzed to obtain pure V-28-3M.

15 Claims, 3 Drawing Sheets

ACETONE ADDUCT OF FUNGICIDAL V-28-3M

This application is a Continuation of International application No. PCT/JP98/04070 Filed on Sep. 10, 1998.

BACKGROUND OF THE INVENTION

The present invention relates to an intermediate for V-28-3M useful as a fungicide, a process for producing it and a process for purifying V-28-3M through the intermediate.

V-28-3M has a high fungicidal activity and a low toxicity. In a previously known method for the purification of V-28-3M in the form of a crude precipitate thereof, after an acid amide or urea is added to an aqueous solution thereof or a solution thereof in a water containing solvent, an insoluble material is removed and an alkali is added to the supernatant to precipitate V-28-3M [Japanese Patent Unexamined Published Application No.5-59084](hereinafter referred to as JP-Kokai 5-59084). However, although the purity of V-28-3M was increased, the crystallization thereof was difficult in this method, and for the further purification, only reversed phase HPLC or counter current distribution method could be employed [Japanese Patent Publication for Opposition Purpose No.4-53878 (hereinafter referred to as JP-Kokai 4-53878)].

In the reversed phase HPLC or counter current distribution method for the high purification, the cost of the purification of the intended product is high because an extremely large amount of the solvent is required for the purification and the quantity of the crude product to be treated each time is only small. Further, the increase in the scale of the laboratory is difficult. Thus, this method is industrially not preferred.

V-28-3M is easily soluble in dimethyl sulfoxide or dimethylformamide, but it is generally difficult to crystallize it from such a polar solvent in which it is highly soluble. Also, although V-28-3M is easily soluble in a water containing solvent such as an aqueous methanol solution, the crystallization thereof from such a solvent is difficult. Methods of recovering V-28-3M from a solution thereof in such a polar solvent in the prior art include a method wherein an extremely large amount of water, for example, 20 parts by volume per part by volume of the solution, is added to the solution, taking advantage of the fact that V-28-3M is practically insoluble in water, or a method wherein an alkali is added to the solution to precipitate V-28-3M at a pH of 12 or above (JP-Kokai 5-59084). However, the precipitate thus obtained could not be crystallized and, therefore, the purity thereof did not reach to the level of that obatined by the HPLC purification method.

SUMMARY OF THE INVENTION

The object of the present invention is to provide an acetone adduct of V-28-3M from which highly pure V-28-3M can be obtained in a high yield.

Another object of the present invention is to provide a process for producing the acetone adduct of V-28-3M.

Still another object of the present invention is to provide a process for purifying V-28-3M by the crystallization to obtain highly pure V-28-3M in a large scale, thereby to make up for the low productivity thereof.

After intensive investigations on the crystallization of V-28-3M, the inventors have found that although V-28-3M is scarcely soluble in ordinary organic solvents, it is slightly soluble in some solvents such as acetone and methanol, particularly in acetone, the crystallization rate of V-28-3M can be remarkably improved and, therefore, the purity thereof can be remarkably increased because the amino sugar moiety of V-28-3M is dehydration-condensed with acetone to form the acetone adduct. The inventors have also found that since the obtained acetone adduct is easily hydrolyzed in an aqueous solution to release acetone, purified V-28-3M can be easily obtained.

In some cases, crude precipitates containing V-28-3M are contaminated with high-molecular substances formed in the course of the culture, which substances inhibit the dissolution of V-28-3M in acetone to lower the recovery rate and also to inhibit the crystallization of the acetone adduct. It has been found that the crystallization of the acetone adduct can be facilitated if V-28-3M precipitate which may be obtained by dissolving the crude precipitate in dimethyl sulfoxide or dimethylformamide and adding an organic solvent to the resulting solution to precipitate only the high-molecular substances, and removing the precipitate, prior to the precipitation of V-28-3M by adding a solvent having lower polarity is used as a starting material for the aceton adduct, because high-molecular substances are removed from the crude precipitate.

The present invention has been established on the basis of these findings.

Namely, the present invention provides a new acetone adduct of V-28-3M represented by following formula (1):

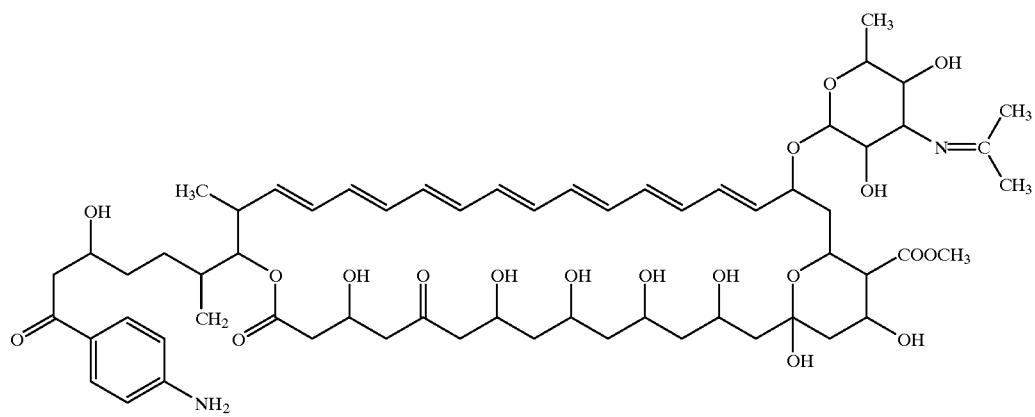

The present invention also provides a process for producing the new acetone adduct of V-28-3M represented by above formula (1), comprising the steps of dissolving a material containing V-28-3M represented by following formula (2) in acetone, concentrating and/or cooling the obtained solution to precipitate and separate impurities from the solution, and concentrating and/or cooling the mother liquor to precipitate the crystals of new acetone adduct of V-28-3M:

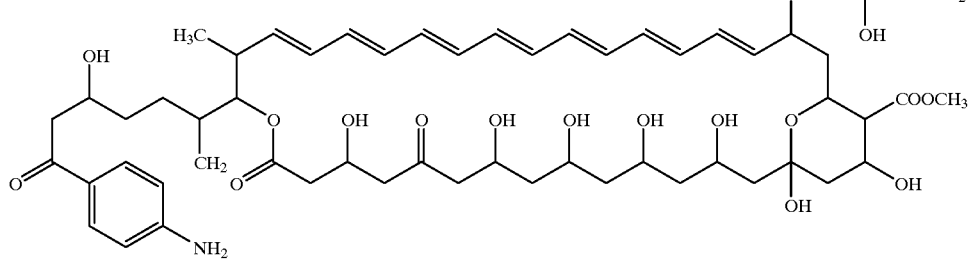

(2)

The present invention also provides a process for purifying V-28-3M, comprising the steps of dissolving the crystals of the acetone adduct of V-28-3M obtained by the precipitation in the above-described production process, dissolving the obtained crystals in a water containing organic solvent to hydrolyze the acetone adduct crystals and thereby obtaining V-28-3M.

DESCRIPTION OF THE PREFERRED EMBODIMENTS

Figure 1:
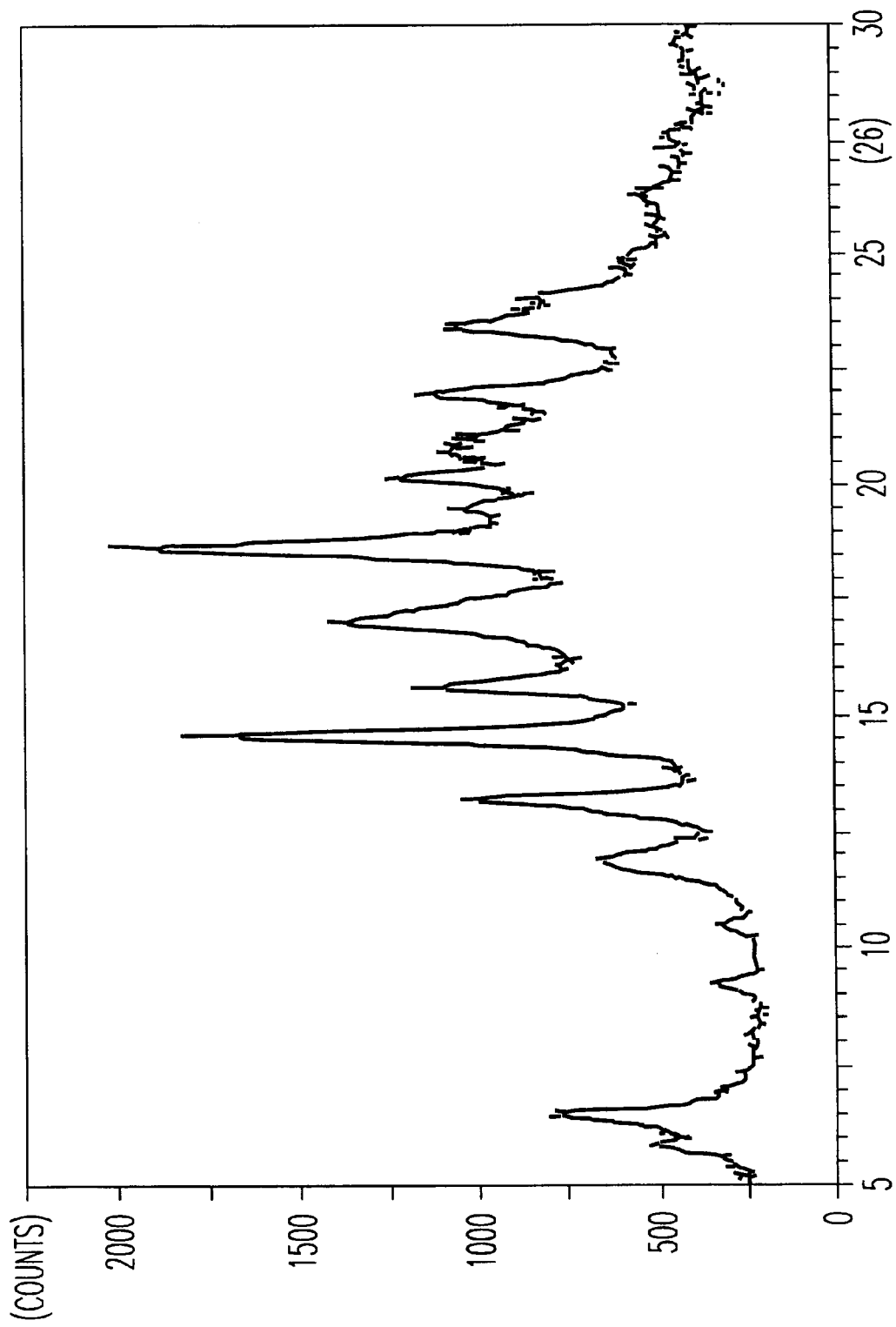
FIG. 1 is a powder X-ray diffraction pattern of an acetone adduct of V-28-3M.

The V-28-3M-containing materials used in the present invention include a solid obtained by drying a reaction solution resulting from methyl-esterified polyene macrolide V-28-3 produced by Streptomyces arenae V-28-3 with diazomethane; a precipitate obtained by adding water to said reaction solution; and a precipitate obtained by the methyl esterification using a compound other than diazomethane, such as a precipitate obtained by protecting the amino group of the amino sugar in V-28-3 with a suitable protecting group and then methyl-esterifying it with, for example, methyl p-toluenesulfonate, removing the protecting group and adding water to the reaction solution (PCT/JP 98/02439). Such a precipitate may contain a large amount of substances derived from the culture or by-products of the reaction.

In the production of the acetone adduct of V-28-3M, the V-28-3M-containing material is dissolved in acetone under heating. The dissolution is conducted at a temperature in the range of 20° C. to the boiling point of acetone, preferably 50 to 57° C. The concentration is preferably in the range of 0.1 to 10 g/l, more preferably 2 to 3 g/l. If necessary, the extraction can be continuously conducted using Soxhlet's extractor.

The concentration of the obtained solution of V-28-3M in acetone is adjusted to 2 to 3 g/l by diluting or concentrating the solution under reduced pressure. The solution is cooled to preferably 10° C. or below, more preferably 0 to −20° C. The precipitate thus formed has a high impurity content. The impurities are preferably separated because they will inhibit the subsequent crystallization of the acetone adduct of V-28-3M. The separation methods include conventional methods such as filtration and centrifugation. After the separation of the precipitate thus formed, the remaining solution is concentrated, if necessary, to control the concentration of the mother liquor in the range of preferably 1 to 20 g/l, more preferably 2 to 4 g/l. Seed crystals are added to the liquid and the obtained mixture is cooled to 20° C. or below to form crystals of the acetone adduct of V-28-3M. The resulting crystals are filtered or centrifuged, washed with acetone and dried under reduced pressure to obtain the crystals of the acetone adduct of V-28-3M having an extremely high purity.

The acetone adduct of V-28-3M thus obtained can be immediately and easily hydrolyzed by dissolving it in a water containing solvent such as acetonitrile+water (1:1). The water containing solvent may be any of water-soluble solvents containing water, such as methanol, ethanol, isopropyl alcohol and acetonitrile. Water preferably contains 0.01 to 1 M of a weak acidic salt having a buffering effect such as ammonium acetate, sodium acetate or sodium phosphate. The acetone adduct of V-28-3M is dissolved in the water containing solvent to obtain a solution having a concentration of preferably 0.1 to 10 g/l, more preferably 1 to 2 g/l. Then the solution is concentrated under reduced pressure to volatilize the solvent and then V-28-3M is precipitates due to its poor solubility. When a salt is dissolved in the water containing solvent, the salting-out effect is also obtained as the solution is concentrated and thus, the precipitate can be easily obtained. After separating the precipitate formed during the concentration by filtration, the precipitate is washed with water or a solvent and then dried under reduced pressure to obtain pure V-28-3M.

When the purity of V-28-3M-containing material is very low, the solubility thereof in acetone decreases or the solution remains supersaturated in the course of the crystallization, which makes the stable crystallization impossible. Therefore, when the purity of V-28-3M-containing material is very low, the purity thereof or of the crude precipitate is preferably increased by the method described below prior to the crystallization.

Namely, the V-28-3M-containing material is dissolved in dimethyl sulfoxide or dimethylformamide, an organic solvent is added to the obtained solution to precipitate impurities in the solution and another organic solvent having a lower polarity is added to the mother liquor to obtain the intended compound as a precipitate.

Specifically, the V-28-3M-containing material is dissolved in dimethyl sulfoxide at room temperature to obtain a solution having a concentration of preferably 1 to 100 g/l, more preferably 10 to 30 g/l. Then a first organic solvent such as ethanol, isopropyl alcohol, n-butanol, ethyl acetate or isopropyl acetate is added in an amount of preferably 1 to 20 parts, more preferably 5 to 10 parts, per part of dimethyl sulfoxide to the solution to precipitate the impurities. After filtration, a second organic solvent having a lower polarity such as n-hexane, n-heptane or toluene is added in an amount of preferably 1 to 20 parts, more preferably 2 to 10 parts, per part of dimethyl sulfoxide to the filtrate to precipitate V-28-3M. The precipitate is collected by filtration, washed with a small amount of a solvent such as a lower alcohol or an acetic ester and then dried under reduced pressure. Thus, the impurities having a hydrophobicity different from that of the intended compound are remarkably reduced in amount and the precipitate having an improved purity can be obtained. Dimethyl sulfoxide can be replaced with dimethylformamide.

The following Examples will further illustrate the present invention.

EXAMPLE 1

1-1. Preparation of N-(9-fluorenylmethoxycarbonyl)-V-28-3:

37.38 g (22.92 mmol) of crude V-28-3 was dissolved in 2.4 liters of a solution of dimethyl sulfoxide/methanol (mixing volume ratio: 9:2). N-(9-fluorenylmethoxycarbonyloxy)succinimide (38.3 g) was added to the solution in four portions at room temperature. The reaction solution was stirred at room temperature for 2 hours and then cooled in an ice bath. 2.4 liters of water was added dropwise to the solution for one hour to obtain the title compound in the form of a slurry. The title compound was separated from the slurry, and washed with 300 ml of water and 500 ml of methanol. The crude precipitate was separated and then dried to obtain 49.28 g (yield: 94%) of crude crystals of the title compound. In the subsequent methyl esterification reaction, the crude crystal was used without purification.

1-2. Preparation of N-(9-fluorenylmethoxycarbonyl)-V-28-3M:

13.5 g (9.5 mmol) of crude N-(9-fluorenylmethoxycarbonyl)-V-28-3 prepared as prepared above was dissolved in 700 ml of a solution of dimethyl sulfoxide/methanol (mixing volume ratio: 9:2) at room temperature. 7.2 ml of methyl p-toluenesulfonate and 1.3 g of potassium carbonate were added to the obtained solution, and the resultant mixture was stirred at 25° C. for 4 hours. Then the reaction solution was cooled to 5° C. and stirred overnight to obtain a reaction solution containing 11.9 g (yield: 93%) of the title compound. The reaction solution was subjected to the deprotection reaction in the subsequent step without isolating the title compound.

1-3. Preparation of V-28-3M:

150 ml of 28% ammonia water (10 v/v% based on the reaction solution) was added to 1500 ml of mixed solvent of dimethyl sulfoxide/methanol (mixing ratio: 9/2) containing 25.8 g (19.3 mmol) of N-(9-fluorenylmethoxycarbonyl)-V-28-3M, prepared as described above, at 25° C., and the obtained mixture was stirred for 2 hours to obtain the reaction solution containing 17.8 g (yield: 82%) of the title compound.

1-4. Preparation of acetone adduct of V-28-3M:

Water was added to the reaction solution containing V-28-3M, prepared as described above, to separate V-28-3M. After separating and drying, 14.8 g of the obtained crude precipitate containing 59% of V-28-3M was dissolved in 0.62 liter of dimethyl sulfoxide at room temperature, and then 4.4 liters of ethyl acetate was added dropwise in the resulting solution under stirring. The precipitate was taken by filtration and 2.6 liters of n-heptane was added dropwise to the filtrate in the same manner as described above. The precipitate thus obtained was taken by the filtration, washed with 0.1 liter of ethyl acetate and dried under reduced pressure to obtain 8.6 g (recovery rate: 80%) of V-28-3M precipitate having a purity of 81%.

Figure 2:
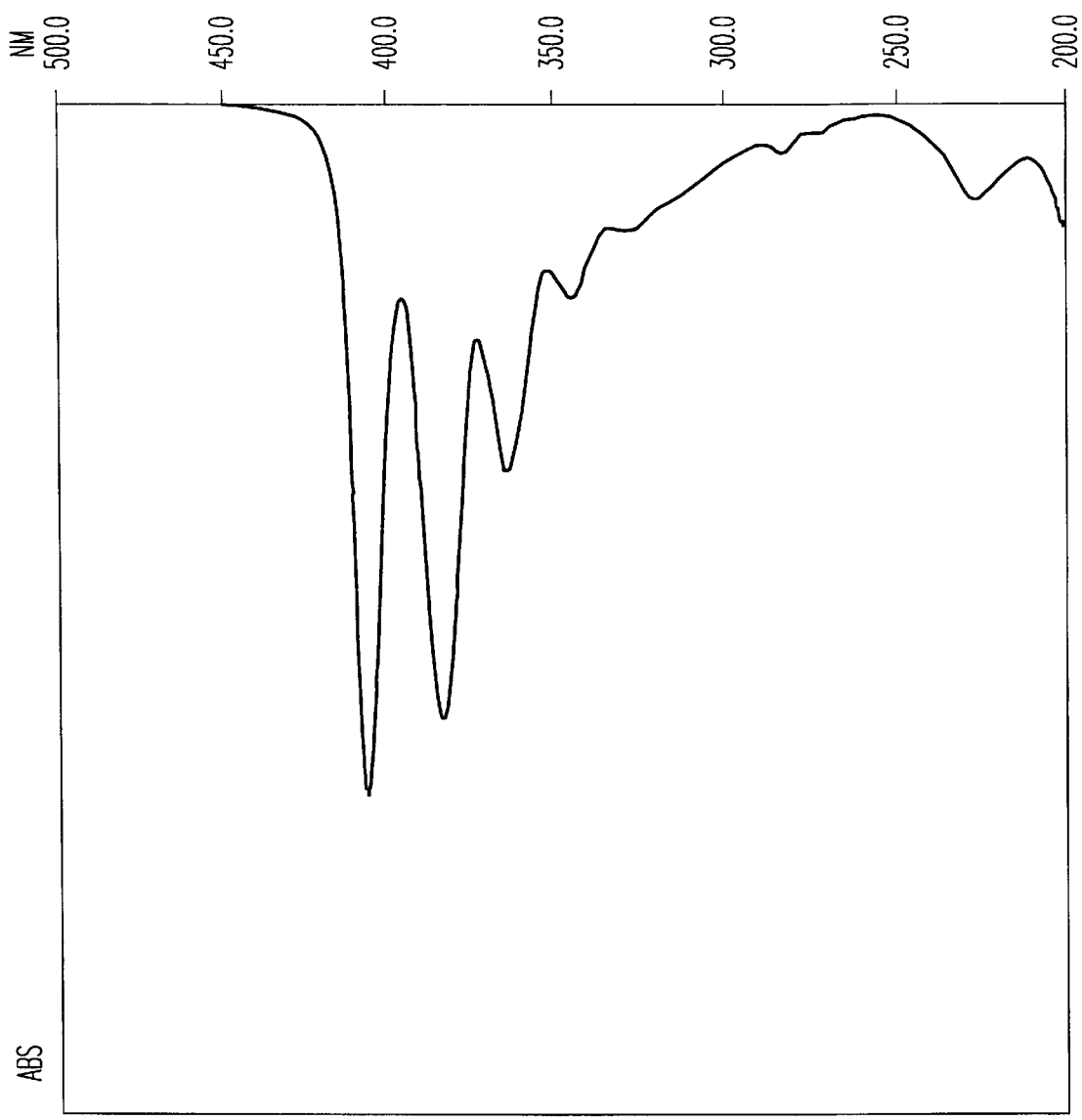
FIG. 2 is a $^1$H-NMR spectrum of the acetone adduct of V-28-3M.
Figure 3:
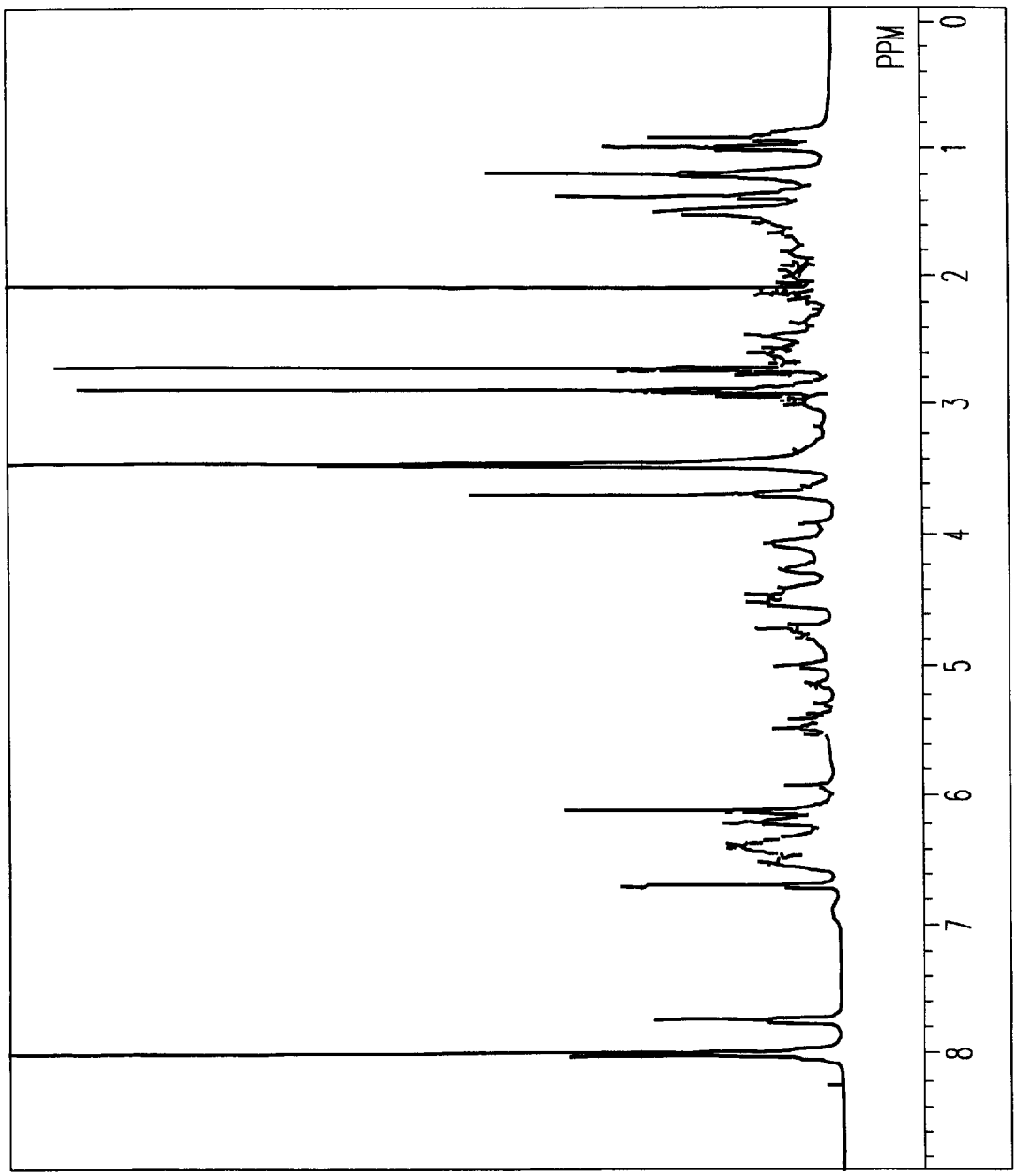
FIG. 3 is a UV absorption spectrum of the acetone adduct of V-28-3M.

4.3 g of the precipitate containing 81% of V-28-3M was dissolved in 1.8 liters of acetone at a boiling point (57° C.) in a continuous extraction tank for 6 hours. The obtained solution was cooled at −10° C. overnight, and the precipitate thus formed was taken by the filtration. The mother liquor was concentrated to a volume of ⅘ under reduced pressure. 30 mg of seed crystals were added to the concentrate. After cooling at −10° C. overnight, the crystals thus formed were taken by the filtration, washed with 100 ml of acetone and dried under reduced pressure to obtain 2.1 g (recovery rate: 60%) of acetone adduct of V-28-3M having a purity of 98% or above. The crystals thus obtained had the following physicochemical properties:

1) Appearance: yellow crystals
2) Mass spectrometric analysis: 1167.8 (FABMS [(M+H)$^+$])
3) Powder X-ray diffraction: as shown in FIG. 1.
4) $^1$H-NMR (determined in DMF-d$_7$): as shown in FIG. 2
  $\delta$7.78 ppm (d, J=8.79, aromatic-H), 6.72 (d, J=8.55, aromatic-H),
  $\delta$3.73 ppm (s, methyl ester), (3.50 (s, acetone adduct part)
  8.05 ppm (DMF), 2.94 ppm (DMF), 2.77 ppm (DMF) and 2.15 ppm (acetone) were solvent signals.
5) UV spectrum (determined in MeOH): as shown in FIG. 3
  $\lambda_{max}$: 363, 382, 405 nm From the above-described physicochemical properties, it was confirmed that the obtained crystals were the acetone adduct wherein the amino sugar moiety of V-28-3M are condensed with acetone.

EXAMPLE 2

Water was added to the same V-28-3M methyl esterification reaction solution as that of Example 1 and then the resultant precipitate was separated and dried to obtain a precipitate containing 49% of V-28-3M. 0.7 g of the precipitate thus obtained was dissolved in 1.0 liter of acetone at 50° C. for 12 hours. The obtained solution was concentrated to a volume of 1/12 under reduced pressure and then cooled at −10° C. overnight. The resultant precipitate was taken by filtration. The mother liquor was concentrated to a volume of ½ under reduced pressure. 2 mg of seed crystals were added to the concentrate, and the obtained mixture was cooled at −10° C. overnight. The crystals thus formed were washed with about 10 ml of acetone and then dried under reduced pressure to obtain 0.08 g (recovery rate: 24%) of acetone adduct of V-28-3M having a purity of 98% or higher. In this Example, the purity of the product was equal to that in Example 1 but the recovery rate was less than that in Example 1. This fact indicates that the higher the purity of the V-28-3M-containing material is, the higher the recovery rate is, which is more useful in the present invention.

EXAMPLE 3

2.1 g of the crystals of the acetone adduct of V-28-3M obtained in Example 1 were dissolved in 1.8 liters of a solution of 50 mM ammonium acetate (pH 5.5)+acetonitrile (1:1) at room temperature, and the obtained solution was concentrated to a volume of ½ under reduced pressure. The precipitates thus formed were collected by centrifugation, washed with ethanol and dried under reduced pressure to obtain 1.5 g (yield: 71%) of purified V-28-3M having a purity of 98% or higher.

The crystal thus obtained had a molecular weight equal to that of V-28-3M determined by MS spectrum, and the $^1$H-NMR pattern of the crystal was the same as that of V-28-3M.

REFERENTIAL EXAMPLE 1

120 mg of crude precipitates containing 50% of V-28-3M was dissolved in 12 ml of dimethyl sulfoxide at room temperature. 96 ml of isopropyl alcohol was added dropwise to the obtained solution under stirring. Then, the precipitates thus formed were taken by filtration, and 108 ml of n-hexane was added dropwise to the filtrate in the same manner as that described above. The precipitates thus formed were taken by filtration, washed with 10 ml of n-hexane and dried under reduced pressure to obtain 41 mg of precipitates of V-28-3M having a purity of 80%.

REFERENTIAL EXAMPLE 2

350 mg of crude precipitates containing 36% of V-28-3M was dissolved in 6 ml of dimethylformamide at room temperature. 12 ml of ethyl acetate was added dropwise to the obtained solution under stirring. Then, the precipitates thus formed were taken by filtration, and 18 ml of n-heptane was added dropwise to the filtrate in the same manner as that described above. The precipitates thus formed were taken by filtration, washed with 5 ml of ethyl acetate and dried under reduced pressure to obtain 118 mg of precipitates of V-28-3M having a purity of 80%.

COMPARATIVE EXAMPLE 1

The HPLC purification was conventionally conducted as follows:

Water was added to a reaction solution obtained by the methyl esterification reaction of V-28-3B as described in JP-Kokai 5-59084. After the separation, the precipitate was dried to obtain 2.5 g of the precipitate containing 50% of V-28-3M, which was then dissolved in 42 ml of dimethyl sulfoxide. 83 ml of a mixture of 50 mM aqueous solution of acetic acid+acetonitrile (1:1) was added to the obtained solution. Then 125 ml of a mixture of 50 mM ammonium acetate (pH 5.7)+acetonitrile (52:48) was added to the obtained mixture and the loading solution was prepared by filtrating out the solid material. 250 ml of the loading solution was passed through a preparative, reversed phase HPLC column YMC ODS R-3101-20, R-3105-50 (100φx (100+500)) at a rate of 30 ml/min, and eluted using 10 liters of a mixture of 50 mM ammonium acetate (pH 5.7)+ acetonitrile (52:48) at a rate of 300 ml/min. About 500 ml of V-28-3M fraction taken according to 280 nm UV absorption pattern was concentrated to a volume of about ½ under reduced pressure, and then left to stand at 4° C. overnight. Precipitates thus formed were collected by centrifugation, washed with water twice and then freeze-dried. 0.6 g (recovery rate: 48%) of V-28-3M having a purity of 86% was obtained.

In this method, the required amount of the solvent is more than 10 times as large as that required for processing the same amount of the starting material according to the acetone adduct crystallization method of Example 1. The productivity in this method was thus extremely low. Further enlargement of the column is required to increase the amount of the preparation, because it is not expected that the loading amount can be further increased for the column used in this method. However, the scale up of the column is technically difficult in general. In addition, the resin packed in the column is very easily degradated when this starting material is used. Since the filling material itself is expensive, the frequent exchange thereof and the large amount of solvent used cause an increase in the cost.

For the reasons described above, the purification with the column has problems in the productivity and the cost.

Thus, the crystallization rate of V-28-3M can be remarkably improved by forming the acetone adduct thereof according to the present invention, and the high purification can be attained without employing the reversed phase HPLC or counter current distribution method wherein a large amount of the solvent is necessitated. Thus, the present invention provides the method of producing V-28-3M using the crystallization process wherein purification can be conducted with relatively smaller amount of the solvent than that of HPLC and the scale up is easier than the column chromatography process, as well as the method of purifying V-28-3M suitable for industrial application wherein a conventional apparatus can be used, which is advantageous in the cost.

What is claimed is:

1. Acetone adduct of V-28-3M represented by formula (1)

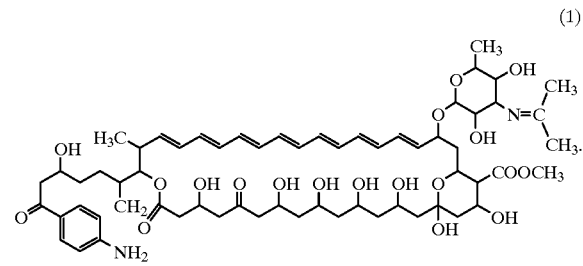

(1)

2. A process for producing the acetone adduct according to claim 1, comprising the steps of dissolving a material containing V-28-3M represented by following formula (2) in acetone, concentrating and/or cooling the obtained solution to precipitate and to separate impurities from the solution, and concentrating and/or cooling the mother liquor to precipitate the crystals of the acetone adduct according to claim 1

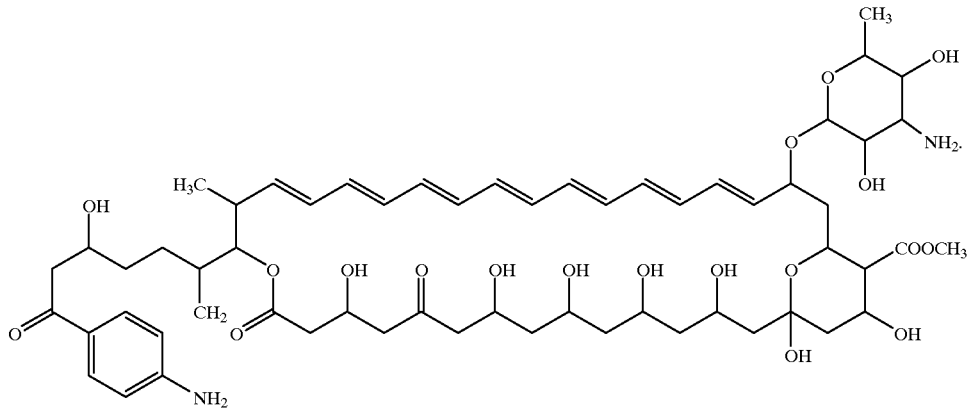

3. The process according to claim 2, wherein the V-28-3M-containing material is dissolved in acetone at a temperature in the range of 20° C. to the boiling point of acetone to obtain a solution having a concentration of 0.1 to 10 g/l, the solution is cooled to 10° C. or below to precipitate and thereby to separate impurities from the solution, the mother liquor is concentrated to a concentration of 1 to 20 g/l, seed crystals are added to the obtained concentrate, and the resultant mixture is cooled to 20° C. or below to form crystals of the acetone adduct.

4. The process according to claim 2, wherein the V-28-3M-containing material is dissolved in dimethyl sulfoxide or dimethylformamide, a first organic solvent is added to the obtained solution to precipitate and thereby to separate impurities from the solution, and a second organic solvent having a lower polarity than the first organic solvent is added to the mother liquor to precipitate V-28-3M to be used as the V-28-3M-containing material.

5. The process according to claim 4, wherein the V-28-3M-containing material is dissolved in dimethyl sulfoxide or dimethylformamide at room temperature to obtain a solution having a concentration of 1 to 100 g/l.

6. The process according to claim 4, wherein the first organic solvent is selected from the group consisting of ethanol, isopropyl alcohol, n-butanol, ethyl acetate and isopropyl acetate.

7. The process stated according to claim 4, wherein the second organic solvent is selected from the group consisting of n-hexane, n-heptane and toluene.

8. A process for purifying V-28-3M, comprising the steps of dissolving a material containing V-28-3M represented by formula (2) in acetone, concentrating and/or cooling the obtained solution to precipitate and thereby to separate impurities from the solution, concentrating and/or cooling the mother liquor to form crystals of the acetone adduct according to claim 1, and dissolving the obtained crystals in a water containing organic solvent to hydrolyze the acetone adduct crystals and thereby to obtain V-28-3M (2)

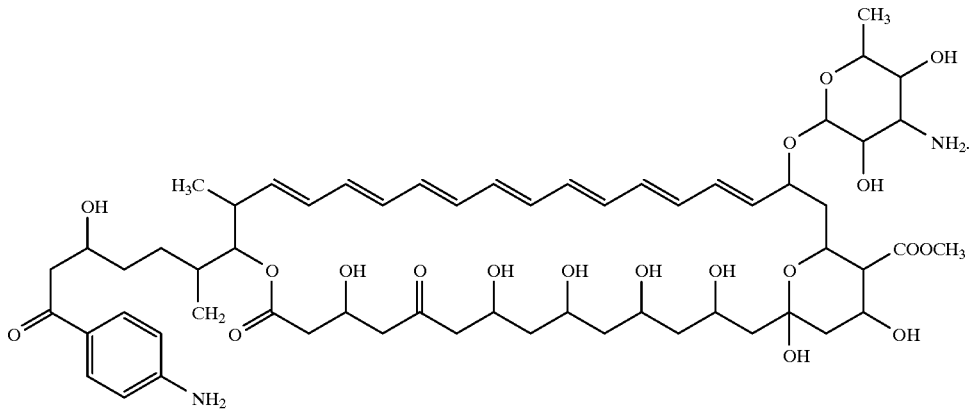

9. The purification process according to claim 8, wherein a solvent selected from the group consisting of water containing methanol, ethanol, isopropyl alcohol and acetonitrile is used as the water containing solvent.

10. The purification process according to claim 9, wherein the water containing solvent contains a weak acidic salt having a buffering effect.

11. The purification process according to claim 10, wherein the weak acidic salt having the buffering effect is selected from the group consisting of ammonium acetate, sodium acetate and sodium phosphate.

12. The purification process according to claim 8, comprising the step of dissolving the V-28-3M-containing material in dimethyl sulfoxide or dimethylformamide, adding a first organic solvent to the obtained solution to precipitate and thereby to separate impurities from the solution, and adding a second organic solvent having a lower polarity than the first solvent to the obtained mother liquor to precipitate V-28-3M.

13. The purification process according to claim 12, wherein the V-28-3M-containing material is dissolved in dimethyl sulfoxide or dimethylformamide at room temperature to obtain a solution having a concentration of 1 to 100 g/l.

14. The purification process according to claim 12, wherein the first organic solvent is selected from the group consisting of ethanol, isopropyl alcohol, n-butanol, ethyl acetate and isopropyl acetate.

15. The purification process according to claim 12, wherein the second organic solvent is selected from the group consisting of n-hexane, n-heptane and toluene.

\* \* \* \* \*